United States Patent [19]

Hsiao

[11] Patent Number: 4,634,587
[45] Date of Patent: Jan. 6, 1987

[54] SUSTAINED RELEASE QUINIDINE DOSAGE FORM

[75] Inventor: Charles H. Hsiao, Cooper City, Fla.

[73] Assignee: Key Pharmaceuticals, Inc., Miami, Fla.

[21] Appl. No.: 641,559

[22] Filed: Aug. 16, 1984

Related U.S. Application Data

[63] Continuation-in-part of Ser. No. 396,669, Jul. 9, 1982, abandoned.

[51] Int. Cl.$^4$ .......................... A61K 9/22; A61K 9/36; A61K 9/52
[52] U.S. Cl. ......................................... 424/19; 424/20; 424/21; 424/22; 424/35
[58] Field of Search ..................... 424/19-22, 424/35

[56] References Cited

U.S. PATENT DOCUMENTS

| | | | |
|---|---|---|---|
| 2,811,483 | 10/1957 | Aterno et al. | 424/21 |
| 2,853,420 | 9/1958 | Lowey | 424/35 |
| 2,887,440 | 5/1959 | Greminger et al. | 424/35 |
| 2,928,770 | 3/1960 | Bardani | 424/35 |
| 3,081,233 | 3/1963 | Enz et al. | 424/20 |
| 3,247,066 | 4/1966 | Milosovich | 424/20 |
| 3,344,029 | 9/1967 | Berger | 424/19 |
| 3,400,185 | 9/1968 | Kohnce et al. | 424/20 |
| 3,632,739 | 1/1972 | Kornblum | 424/20 |
| 3,773,920 | 11/1973 | Nakamoto et al. | 424/19 |
| 3,835,221 | 9/1974 | Fulberth et al. | 424/20 |
| 3,907,983 | 9/1975 | Seth | 424/35 |
| 3,917,813 | 11/1975 | Pedersen | 424/20 |
| 3,922,339 | 11/1975 | Shear | 424/19 |
| 4,016,254 | 4/1977 | Seager | 424/271 |
| 4,083,949 | 4/1978 | Benedikt | 424/20 |
| 4,138,475 | 2/1979 | McAinsh et al. | 424/20 |
| 4,173,626 | 11/1979 | Dempski et al. | 424/20 |
| 4,248,858 | 2/1981 | Guley et al. | 424/21 |
| 4,259,314 | 3/1981 | Lowey | 424/19 |
| 4,321,253 | 3/1982 | Beatty | 424/35 |
| 4,341,759 | 7/1982 | Bogentoft et al. | 424/21 |
| 4,384,004 | 5/1983 | Cea et al. | 426/3 |
| 4,508,702 | 4/1985 | Hsiao | 424/19 |
| 4,555,399 | 11/1985 | Hsiao | 424/35 |

FOREIGN PATENT DOCUMENTS 109438  1/1940  Australia .............................. 424/20

*Primary Examiner*—Shep K. Rose
*Attorney, Agent, or Firm*—Warrick E. Lee, Jr.

[57] ABSTRACT

A sustained release quindine dosage form is made from a plurality of pellets. Each pellet includes a quinidine-containing coating over a nonpareil seed, with a further coating of about 5 to about 15% by weight of a mixture of about 1.5 to about 9 parts by weight ethylcellulose to about 1 part by weight hydroxypropylcellulose.

6 Claims, No Drawings

SUSTAINED RELEASE QUINIDINE DOSAGE FORM

This application is a continuation-in-part of my co-pending application Ser. No. 396,669, filed July 9, 1982 now abandoned.

Quinidine is a well known alkaloid used in the treatment of certain cardiac arrhythmias. It is a general cardiac depressant, which reduces myocardial excitability, automaticity and conductivity.

In accordance with the present invention there is provided a sustained release quinidine dosage form which comprises a plurality of pellets having an average diameter greater than about 1 mm. Each pellet has a coating of a quinidine over nonpareil seed. The quinidine-coated nonpareils are then coated with a mixture of about one and one half to about nine parts by weight ethylcellulose to about one part by weight hydroxypropylcellulose. Each pellet is coated to about 5–15% of its weight with that coating mixture.

In one embodiment, the present invention provides a sustained release quinidine dosage form, as a capsule containing from about 200 to about 600 of the polymer-coated pellets. In another embodiment, pellets are compressed to a tablet.

The nonpareils, typically sugar seeds having a mesh size of about 20 to about 25, are coated with more than an equal amount by weight of a quinidine compound, which preferably is quinidine bisulfate. In a preferred embodiment, about two parts by weight quinidine bisulfate are coated onto one part by weight of nonpareil seeds. In one embodiment, 500 gm nonpareil seeds are placed in a coating pan and wetted with a 30% sucrose solution with the aid of a sprayer. Approximately 30 gm of quinidine bisulfate are dusted onto the thus-treated pellets, distributing the material manually as necessary. Wetting and dusting procedures are repeated until a buildup of 1000 gm of quinidine bisulfate takes place per 500 gm of the nonpareils.

When coated with a greater than equal weight of quinidine, the thus quinidine-coated nonpareil seeds are coated with a sustained release polymeric coating mix, which comprises from about one and one half to about nine parts by weight of ethylcellulose, an ethyl ether of cellulose, to about one part by weight hydroxypropylcellulose, wherein the primary hydroxyls present in cellulose have been substituted (etherified) by hydroxypropyl. When the pellets are coated with about 5–15% by weight of the coating mixture, the presence of 20–40% by weight of the more water-soluble hydroxypropylcellulose in the outer coating provides "channels" for the water to enter and, over a period of time, leach out the quinidine disposed on the nonpareil seed. The presence of too many "channels", more than 40% by weight of hydroxypropylcellulose, will make the quinidine more rapidly available than therapeutically appropriate unless an excessive amount of coating is applied. Too few channels, less than 20% by weight of hydroxypropylcellulose, results in a loss of the constant or linear release characteristics of the dosage form. Within the stated range, an optimal release rate is obtained when the outer coating contains 7 parts of ethylcellulose to 3 part of hydroxypropylcellulose.

EXAMPLE 1

In one embodiment, 700 gm of quinidine bisulfate-nonpareils (2:1 weight ratio), produced above, are charged into an air suspension coating column (Wurster column, six inches, manufactured by Glatt Air Techniques) and after commencement of the air suspension of these pellets, there is charged into the air suspension a spray of methanol-chloroform (311 ml methanol; 1245 ml chloroform) which contains 77.8 gm mixture of ethylcellulose (Ethocel type 10, Dow Chemical Co.) and hydroxypropylcellulose (Klucel LF, Hercules), this mixture having a weight ratio of 7 parts ethylcellulose to 3 parts hydroxypropylcellulose.

Typical conditions useful for preparing the polymeric coating of the pellets in the above-described equipment include a 40° C. inlet temperature, 2 bar spray air pressure and a liquid feed rate of 12 cc per minute.

Pellets produced in accordance with the procedure (s) set forth above yield a sustained release over a prolonged period of time. When tested according to U.S.P. XX dissolution procedure (one hour in simulated gastric fluid followed by simulated intestinal fluid) the following release characteristics were noted:

| Time (hrs.) | % Release |
|---|---|
| 1 | 15.3 |
| 2 | 29.5 |
| 4 | 58.2 |
| 6 | 86.4 |
| 8 | 99.6 |

This example illustrates that when 30% of hydroxypropylcellulose is present in the coating, quinidine is released constantly over a long period of time, making the pellet suitable for use as a long-acting, sustained-release dosage form.

EXAMPLE 2

Using a procedure similar to that of Example 1, but with a 3% by weight coating, quinidine bisulfate-nonpareils were coated with 80% ethylcellulose 20% hydroxypropylcellulose. When tested according to the U.S.P. XX dissolution procedure, as in Example 1, the following release characteristics were observed:

| Time (hrs.) | % Release |
|---|---|
| 1 | 27.5 |
| 2 | 54.4 |
| 3 | 70.2 |
| 4 | 80.0 |
| 6 | 91.2 |
| 8 | 98.6 |

EXAMPLE 3

Using a procedure similar to that of the previous examples, but with a 5% by weight pellet coating, quinidine bisulfate-nonpareils were coated with 80% ethylcellulose-20% hydroxypropylcellulose. When tested according to the U.S.P. XX dissolution procedure, the following release characteristics were observed:

| Time (hrs.) | % Release |
|---|---|
| 1 | 9.4 |
| 2 | 24.1 |
| 3 | 34.4 |
| 4 | 43.8 |
| 6 | 59.8 |
| 8 | 72.1 |

| Time (hrs.) | % Release |
|---|---|
| 10 | 82.4 |

EXAMPLE 4

Quinidine bisulfate-nonpareils were coated with 7% of the same coating mixture utilized in Examples 2 and 3. When tested according to the U.S.P. XX dissolution procedure, the following release characteristics were observed:

| Time (hrs.) | % Release |
|---|---|
| 1 | 4.7 |
| 2 | 15.9 |
| 3 | 22.6 |
| 4 | 28.6 |
| 6 | 40.4 |
| 8 | 50.7 |
| 10 | 61.8 |

Examples 2 and 3 illustrate that when 20% or less by weight of hydroxypropylcellulose is used in the coating, the pellets tend to lose their constant or linear release characteristics. Thicker coating, as in Example 4, makes the release rate more constant, but the release rate becomes too slow to be desirable.

The pellets of the present invention may be provided in a container, such as a capsule, or compressed, optionally with the addition of a tabletting aid such as magnesium stearate. The capsule embodiment of the present invention is particularly advantageous for pediatric and geriatric patients who may be either unable or unwilling to swallow a larger sustained release tablet. For pediatric administration it is particularly contemplated that the individually coated polymeric pellets are administered in food.

What is claimed:

1. In a sustained release quinidine dosage form which comprises a compressed tablet or capsule, the improvement consisting essentially of plurality of pellets, the average pellet diameter greater than about 1 mm, each pellet consisting essentially of a coating of quinidine over a nonpareil seed, the thus quinidine-coated nonpareils are coated thereon with a coating consisting essentially of about 5% to about 15% by weight of a mixture of about 1.5 to about 9 parts by weight ethylcellulose to about 1 part by weight hydroxypropylcellulose, the sum of such pellets in forming a single dosage unit of quinidine.

2. A sustained release quinidine dosage form of claim 1 wherein said quinidine is in the form of quinidine bisulfate.

3. A sustained release quinidine dosage form of claim 1 wherein the coating consisting essentially of 2.3 parts by weight ethylcellulose per part of hydroxypropylcellulose.

4. A sustained release quinidine dosage form of claim 1 wherein the weight of quinidine is approximately twice that of the nonpareil.

5. A sustained release quinidine dosage form of claim 1 wherein said container is a capsule.

6. A sustained release quinidine dosage form of claim 1 where in the plurality of pellets are compressed into a tablet.

* * * * *